(12) United States Patent
Huegli

(10) Patent No.: US 7,195,609 B2
(45) Date of Patent: Mar. 27, 2007

(54) PISTON STOPPER FOR INJECTION DEVICE, PRODUCT CONTAINER AND INJECTION DEVICE

(75) Inventor: Serge Huegli, Kirchberg (CH)

(73) Assignee: Disetronic Licensing AG, Burgdorf (CH)

( * ) Notice: Subject to any disclaimer, the term of this patent is extended or adjusted under 35 U.S.C. 154(b) by 622 days.

(21) Appl. No.: 10/461,297

(22) Filed: Jun. 13, 2003

(65) Prior Publication Data

US 2003/0233075 A1 Dec. 18, 2003

(30) Foreign Application Priority Data

Jun. 14, 2002 (DE) .................. 102 26 643

(51) Int. Cl.
*A61M 31/00* (2006.01)

(52) U.S. Cl. .................. 604/67; 604/222; 604/181

(58) Field of Classification Search ............ 604/65–67, 604/218–222, 181, 187, 228, 121, 141, 226, 604/230

See application file for complete search history.

(56) References Cited

U.S. PATENT DOCUMENTS

| 4,931,043 | A | * | 6/1990 | Ray et al. .................. 604/228 |
| 5,735,825 | A | | 4/1998 | Stevens et al. |
| 5,808,203 | A | * | 9/1998 | Nolan et al. .................. 73/700 |
| 6,090,081 | A | * | 7/2000 | Sudo et al. .................. 604/230 |
| 2003/0073954 | A1 | * | 4/2003 | Moberg et al. ............. 604/154 |

FOREIGN PATENT DOCUMENTS

| DE | 27 15 696 | 10/1977 |
| DE | 695 02 357 T2 | 1/1999 |
| DE | 695 16 718 T2 | 11/2000 |
| EP | 0 635 278 A1 | 1/1995 |

* cited by examiner

*Primary Examiner*—Nicholas Lucchesi
*Assistant Examiner*—Theodore J. Stigell
(74) *Attorney, Agent, or Firm*—Dorsey & Whitney, LLP

(57) ABSTRACT

The invention relates to a piston stopper for an injection device, for injecting a medical or therapeutic product by axially advancing a piston stopper into a product container, wherein the piston stopper includes a stopper body and a stopper body holder detachably connected to it, and wherein a membrane body is placed like a cap onto the stopper body and connected to it, the membrane body being formed from an elastic material, while the stopper body and the stopper body holder are manufactured from an inflexible material. The invention encompasses an embodiment wherein the stopper body holder supports a sensor which measures the pressure acting on the membrane body to enable the pressure to be monitored precisely, in order to detect leaks and blockages in injection devices.

16 Claims, 10 Drawing Sheets

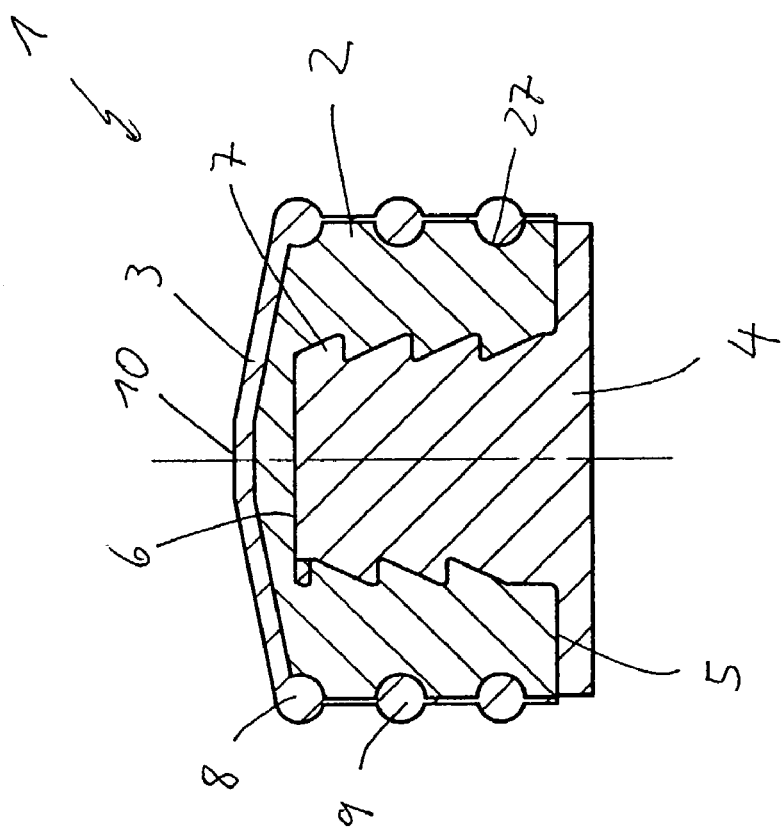
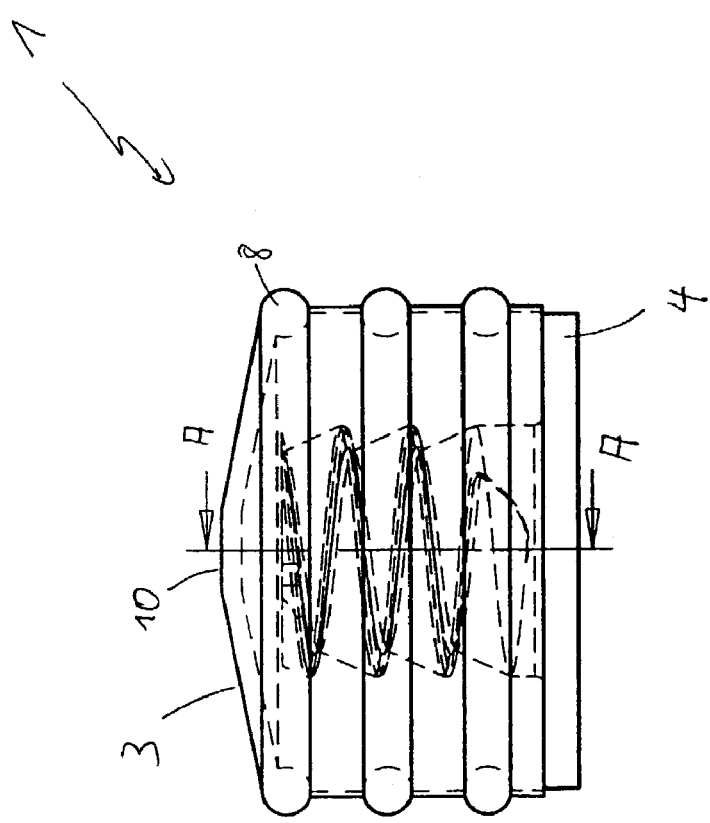
Fig. 1

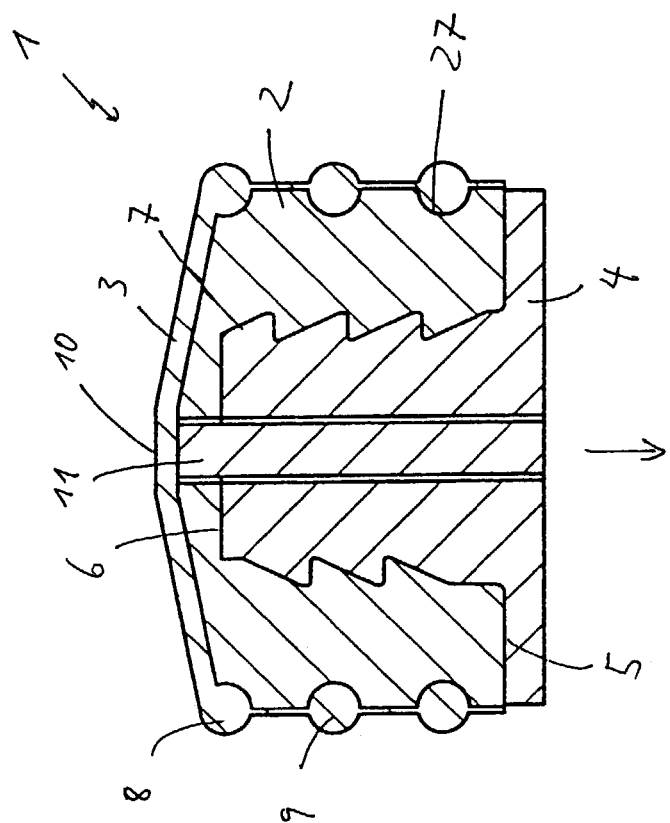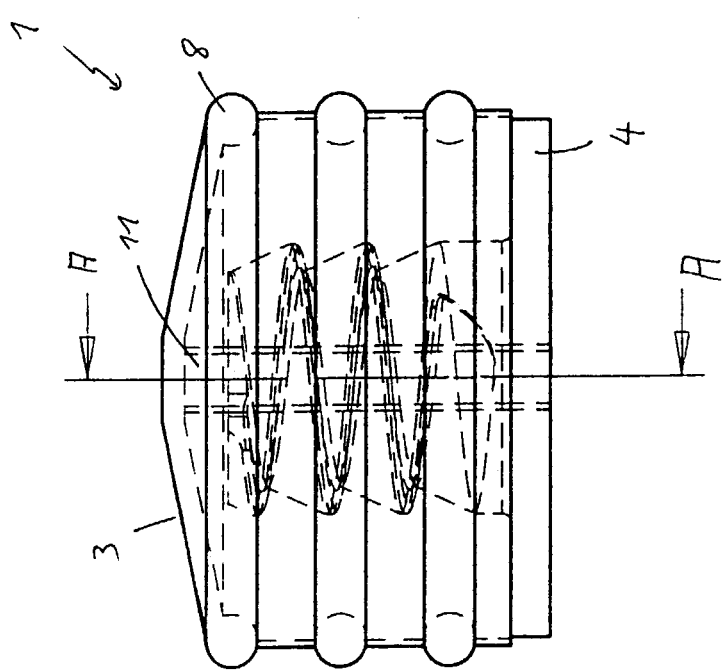
Fig. 2

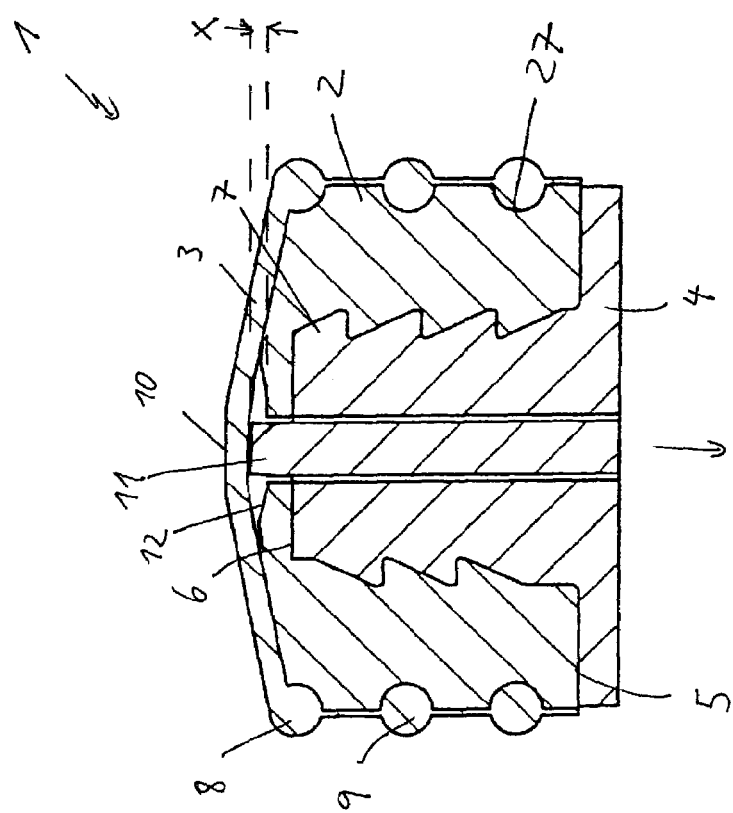
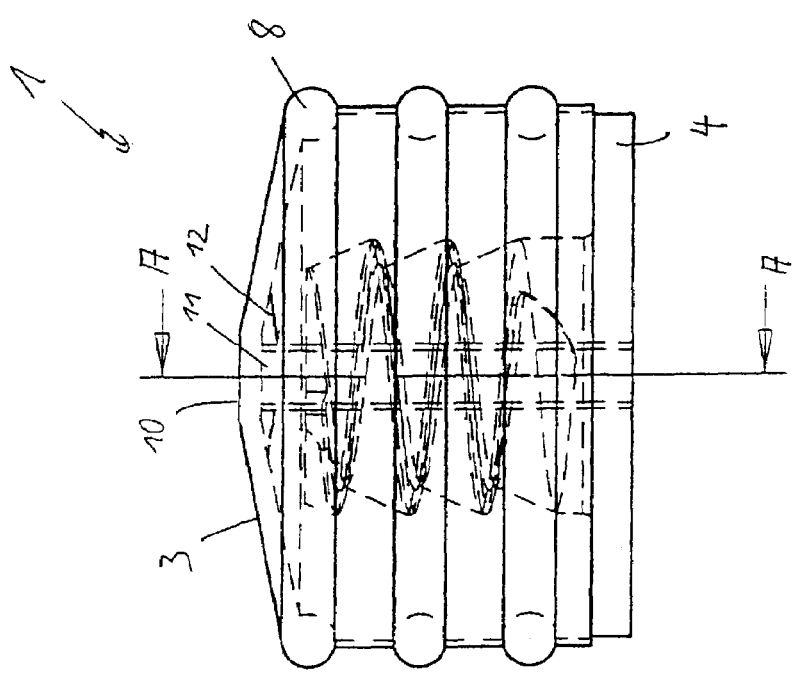
Fig. 3

PISTON STOPPER FOR INJECTION DEVICE, PRODUCT CONTAINER AND INJECTION DEVICE

CROSS-REFERENCE TO RELATED APPLICATIONS

This application claims priority to German Application 102 26 643.3, filed on Jun. 14, 2002, the contents of which are incorporated by reference herein.

BACKGROUND

The present invention relates to injection devices and methods of injecting medicinal products. More particularly, it relates to a piston stopper for injection devices, which serve to inject a medical or therapeutic product, and to product containers for such a medical or therapeutic products. Further, it relates to product containers and injection devices, each comprising a piston stopper in accordance with the invention. The application claims the priority of German patent application No. 102 26 643.3, filed on Jun. 14, 2002 with the German Patent and Trademark Office.

Piston stoppers of a generic type are known. For example, the piston stopper of DE 33 25 622 A1 is inserted into a syringe cylinder serving as a product container for the product to be injected, for example a liquid comprising a medical or therapeutic active agent. If the piston stopper is axially advanced into the product container, then the product to be injected is forced out through a delivery opening at the proximal end of the product container, where an injection needle is usually attached. The piston stopper comprises a stopper body holder which supports a stopper body which is in direct contact with the product stored in the product container and which seals off the product container. For the piston stopper to have a sealing fit in the product container, the stopper body is formed from an elastic material which is circumferentially supported against the inner circumference of the product container. The outer dimensions of the stopper body are slightly larger than the inner dimensions of the product container, such that the stopper body fits in the product container, sealed by elastic distortion.

The necessary elasticity of the stopper body causes a certain inertia in the response characteristics of the piston stopper. It does not respond immediately when a force is applied to axially advance the piston stopper. Until the static frictional force is exceeded, the applied forces predominantly result in a distortion of the stopper body, but not a delivery of the product to be injected. Thus, although a driven member of the injection device which advances the stopper body is axially advanced towards the product container, product is not delivered. When the static frictional force is exceeded, the elastic distortion is initially partially reduced since the sliding friction between the stopper body and the inner wall of the product container is typically smaller than the static friction. If the amount of product actually delivered from the product container over time and the actual adjusting path of the driven member of the injection device are plotted, peaks are identified which are difficult to control, in particular in micro-dosing. These peaks affect precision, in particular in micro-dosing systems in which the product to be injected is to be administered quasi-continuously in a multitude of relatively small doses over an extended period of time. The height of the peaks observed has an effect on the minimum achievable individual dose of an injection device or such a micro-dosing system.

The inertia in the response characteristics caused by the elasticity of the stopper body is also disadvantageous in the event of a blockage in areas downstream of the injection device, for example in blockages in the injection needle or in hoses arranged downstream, since it is possible to inadvertently deduce from an actually observed adjustment of the driven member of the injection device that a product has been delivered, although no product has actually been delivered due to the blockage, rather the stopper body has merely been distorted.

SUMMARY

It is an object of the present invention to provide a piston stopper which addresses the aforementioned disadvantages of the prior art. In particular, the intention is to develop a piston stopper suitable to replace the generic type, to the effect that it is easily possible to precisely dose and monitor the administered dosage. In accordance with another aspect of the invention, the intention is to provide a piston stopper which enables the pressures actually occurring while a product is delivered to be easily monitored. In addition, the intention is to provide a corresponding product container and an injection device which enable easy and precise dosing.

These objects are addressed by a piston stopper for an injection device, for injecting a medical or therapeutic product by axially advancing said piston stopper into a product container, comprising a stopper body, a stopper body holder which can be or is connected to a driven member of said injection device, and at least one sealing element for sealing off said product container from said stopper body, wherein a membrane body is placed like a cap onto a proximal end of the stopper body and connected to it, such that the stopper body does not come in contact with the product to be injected. The membrane body comprises said at least one sealing element. The objects are further addressed by a product container for an injection device for administering a medical or therapeutic product, comprising a piston stopper as set forth above which may be axially slid in the product container, in order to force out the product, and by an injection device for administering a medical or therapeutic product, comprising a piston stopper as set forth above which can be axially advanced into a container for the product to be administered, in order to force out the product.

In accordance with the present invention, a piston stopper comprises a stopper body, a stopper body holder which is preferably detachably connected to the stopper body and supports the stopper body, and a membrane body which is placed onto and connected to a proximal end of the stopper body in the manner of a cap, such that the stopper body itself does not come in contact with the product to be injected when the piston stopper is inserted into a product container storing a product to be injected. The membrane body comprises at least one sealing element for sealing the product container off from the stopper body when the piston stopper is inserted into the product container.

In accordance with one embodiment of the invention, the membrane body covers the proximal end of the stopper body, which is substantially adapted to the inner cross-section of the product container, and the outer circumference of the stopper body, which faces the inner wall of the product container, at its proximal end. In one embodiment, the proximal end of the stopper body is substantially completely covered by the membrane body and therefore does not come in direct contact with the product stored in the product container.

In one embodiment, the membrane body provided in accordance with the invention provides an additional degree of freedom in the design of piston stoppers and/or containers for medical or therapeutic products, because only the membrane itself, and not the stopper body or the stopper body holder, comes in contact with the medical or therapeutic product. Therefore, in accordance with the invention, only the membrane body itself needs to be manufactured from a material which is compatible with medicines and/or is officially approved or compatible for the medical or therapeutic product stored in the product container. The stopper body itself and/or the stopper body holder can thus be manufactured from materials which are not compatible with medicines and/or officially approved for the product. It must be taken into account here that in medicine containers—for example, ampoules—strict legal regulations have to be kept to with regard to sterility, etc. In the case of medical apparatus, all the individual components usually have to be officially approved, such that exchanging individual components is immediately permissible.

Due to the substantially two-part design of a piston stopper in accordance with the invention, which consists on the one hand of the stopper body connected to the membrane body and on the other of the stopper body holder, the stopper body holder can easily be exchanged in accordance with the invention, without infringing official approval or legal regulations. Since the sealing element seals off the product container not only fluid-proof but also sterilely, components arranged downstream of the stopper body, such as the stopper body holder, are not important for keeping to official approval regulations and legal regulations.

In one embodiment, the membrane body preferably forms a comparatively thin cover on the proximal end of the stopper body. Advantageously, the membrane body is only slightly distorted elastically due to its low volume, such that the piston stopper in accordance with the invention immediately responds to an axial adjustment of the stopper body, without the aforementioned peaks in the dosing of the product to be delivered. The negligible inertia of a piston stopper in accordance with the invention thus enables the actually administered dosage to be precisely dosed and monitored. Also, any blockages can be more quickly detected, since elastic distortion is diminished or prevented.

The substantially two-part design of the piston stopper in accordance with the invention also allows the stopper body holder itself to be made and adjusted with high precision. For this purpose, in one embodiment, the stopper body holder is preferably detachably connected to the stopper body supporting the membrane body. If the product container is empty after the product has been administered, then the preferably high-precision stopper body holder can be detached from the stopper body, for example by turning or releasing a latching connection, and disposed of with the empty product container. Once the stopper body holder has been connected to the stopper body of a new product container, the injection device is available again for a new injection.

In one embodiment, the at least one sealing element for sealing the product container off from the stopper body is preferably formed on the outer circumference of the membrane body, for example in the form of a circumferential swelling, in the form of wedge-shaped structures protruding from the outer circumference, etc. The area of the membrane body actually in contact with the product stored in the product container can thus be formed advantageously thinly. Only the sealing elements themselves are formed comparatively thickly, in order to seal the product container off by elastic distortion and pressing against the inner circumference of the product container.

In one preferred embodiment, the stopper body—preferably also the stopper body holder—is manufactured from an inflexible material, in particular from an inflexible plastic material. An exemplary material is polypropylene. The membrane body itself is by contrast preferably completely or at least partially formed from an elastic material. One preferred material is, in particular, bromobutyl caoutchouc.

At its proximally front end which abuts the front facing area of the stopper body, the membrane body can in principle also be manufactured from an inelastic material. In this embodiment, however, the membrane body is formed from an elastic material at least on the sections forming the at least one sealing element on the outer circumference. Thus, the membrane body can also be formed from materials or material sections having different elasticities.

In accordance with a preferred embodiment, the inner diameter of the membrane body is smaller in its resting state than the outer diameter of the proximal end of the stopper body, onto which the membrane body is placed. Thus, when placed cap-like onto the proximal end of the stopper body, the membrane body is expanded, which biases or distorts the membrane body on its proximal facing area which is placed onto the proximal end of the stopper body. Due to the bias, the proximal facing side of the membrane body is thus advantageously less elastic, which increases the precision in dosing and monitoring the actually administered dose even further.

In one preferred embodiment, the sealing element is formed as a swelling on the outer circumference of the membrane body, extending in the circumferential direction of the membrane body, for example as a circumferential bulge which engages with a corresponding circumferential indentation provided on the outer circumference of the stopper body. The membrane body placed onto the proximal end of the stopper body can thus automatically be connected to the stopper body in an advantageously simple way, by simply pushing it on. The holding force of the sealing elements in the circumferential indentations is preferably selected such that, even when it is radially expanded as mentioned above, the membrane body reliably fits on the stopper body.

In accordance with another aspect of the present invention, the aforementioned piston stopper additionally comprises a sensor to detect the prevailing pressure at the proximal end of the membrane body, for example, the pressure exerted on the product stored in the product container. The aforementioned, substantially two-part design of the piston stopper in accordance with the invention is thus utilized, in order to integrate a pressure, force or adjusting path sensor simply into the piston stopper. In one embodiment, the sensor, or a subtle force transferring means conducting a pressure force onto the sensor, preferably directly abuts an inner area of the membrane body and transfers a force or adjusting movement onto the detecting sensor. Since the membrane body is formed, at least on its proximal facing side, as a comparatively thin cover of the stopper body, the prevailing forces there are transferred unaltered, and substantially without the membrane body distorting, onto the sensor. In this way, pressure forces can be detected very precisely.

Since in some embodiments, the stopper body and/or the stopper body holder are preferably manufactured from an inflexible material, these elements are not distorted, such that the forces or adjusting paths measured are not altered by other components of the piston stopper distorting.

In one preferred embodiment, the stopper body holder comprises the sensor. The sensor may be integrated into and/or fixedly connected to the stopper body holder, respectively. Due to the substantially two-part design of the piston stopper in accordance with the invention as described above, the stopper body holder together with the sensor can be separated from the rest of the piston stopper and/or from the product container in a comparatively simple way. The stopper body holder and/or the sensor can advantageously be made to a comparatively high grade, while the stopper body and/or the product container may be designed as simple disposable articles.

In some embodiments, the stopper body preferably comprises an axial opening, in particular on the longitudinal axis of the stopper body, such that the sensor or the force transferring means can directly abut the inner side of the membrane body, in order to directly transfer the prevailing pressure there onto the sensor.

In accordance with one variant, the sensor is formed as a pressure sensor and the proximal end of the stopper body holder comprises an axial continuation which substantially protrudes through the opening in the stopper body, such that the pressure sensor directly abuts the inner side of the membrane body.

In accordance with another variant, the sensor can be arranged in an axial receptacle, for example a cylindrical bore, of the stopper body holder. An elongated and axial movable force transferring means is held in the receptacle, said force transferring means protruding through the opening of the stopper body and abutting the inner side of the membrane body. The distortion of the membrane body is thus transferred directly onto the sensor.

In accordance with other variants, the force transferring means can also transfer the force onto a fluid-filled chamber situated in the stopper body holder, in which chamber a pressure sensor detects the change in pressure caused by the axial adjustment of the force transferring means. In accordance with another embodiment, the sensor measures an axial adjustment of the force transferring means when the membrane body is distorted.

In accordance with one preferred embodiment, the stopper body and the stopper body holder can be rigidly connected to each other, to which end a connecting means for connecting the stopper body to the stopper body holder is provided on the proximal end and/or on the outer circumference of the same. This connecting means may be a simple screw or latch mechanism which can be engaged and disengaged, for example by turning the stopper body and the stopper body holder relative to each other.

In one embodiment, the force transferring means may be accommodated in the stopper body holder, at least secured against rotation, and also secured against loss, such that when the connection between the stopper body holder and the stopper body is released, the force transferring means remains connected to the stopper body holder and no forces or only slight forces are transferred onto the sensor, which forces could result in the sensor separating from the stopper body holder.

A piston stopper in accordance with one aspect of the present invention thus enables the actually administered dosage in injection devices to be precisely dosed and monitored simply. One preferred application relates to injection or infusion devices for administering medical active agents, for example insulin in the case of diabetic patients. The injection device can be hand-operated. The product can, however, also be dosed motor-controlled, for example with the aid of a motor-adjustable driven member.

In some embodiments, a pressure monitoring means is preferably provided in such an injection device, for monitoring the pressure or adjusting path detected by the sensor. The pressure or adjusting path detected by the sensor can be compared with a pre-settable threshold value. In quasi-continuously operating micro-dosing injection or infusion devices, a warning means can be provided which generates a warning signal for the user when the pressure or adjusting path detected exceeds or falls below the pre-settable threshold value.

BRIEF DESCRIPTION OF THE DRAWINGS

Embodiments of the present invention, including preferred embodiments, will now be described by referring to the accompanying drawings, in which:

FIG. 1 shows a piston stopper in accordance with one embodiment of the present invention, in a side view and a cross-section;

FIG. 2 shows a piston stopper in accordance with a second embodiment of the present invention, in a side view and a cross-section;

FIG. 3 shows a modification of the piston stopper in accordance with FIG. 2, comprising an indentation on the proximal end of the stopper body;

In the figures, identical reference numerals indicate identical or functionally identical elements or sub-assemblies.

DETAILED DESCRIPTION

Figure 4:
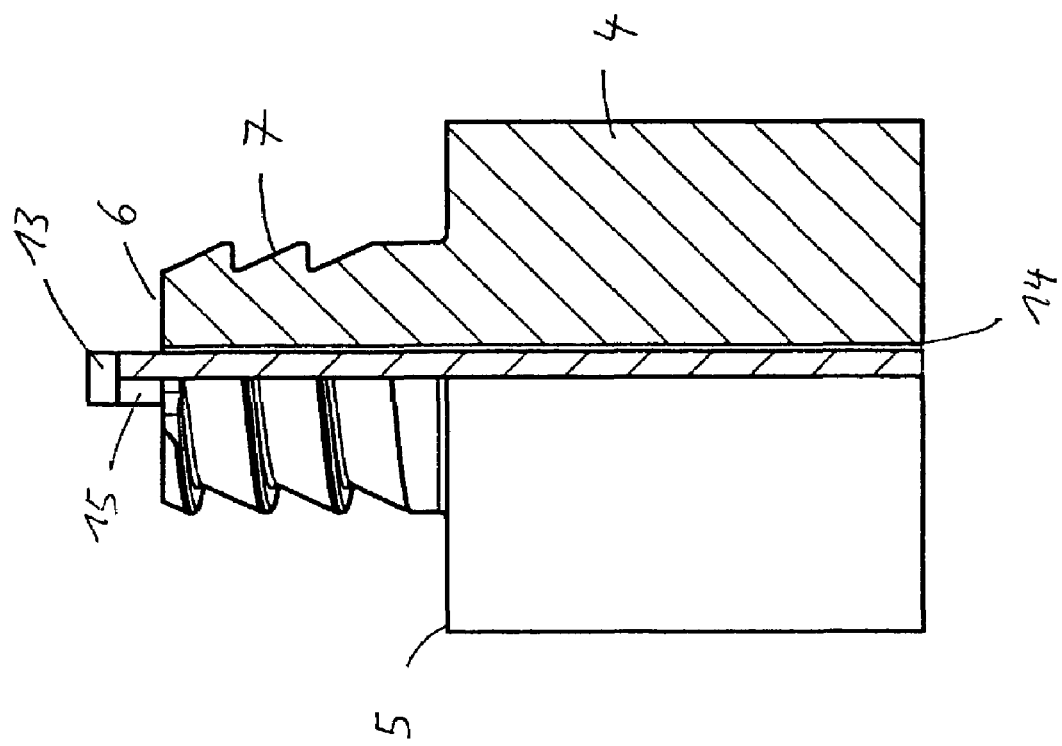
FIG. 4 shows a stopper body holder in accordance with the second embodiment, in a schematic cross-section.

FIG. 1 shows a side view and a cross-section of a piston stopper in accordance with one embodiment of the present invention. The piston stopper comprises a stopper body 2, onto which the membrane body 3 is placed like a cap, and connected to it. The stopper body is inserted into a product container at the distal end, i.e., the end facing away from the delivery opening, of the product container. By axially advancing the piston stopper 1, the product to be injected is then delivered from a delivery opening provided at the proximal end of the product container.

The stopper body 2 is rigidly connected to the proximal end of the stopper body holder 4 by means of connecting means 7, shown schematically. The stopper body holder 4 is in turn connected to a drive member of an injection device (not shown), for example a plunger, abuts the same at least at the time of delivering the product or is formed together with it as one piece. A screw connection, a latching connection or the like can serve as the connecting means 7. The stopper body 2 can thus be detached from the stopper body holder 4. Preferably, the connection is released by turning the stopper body holder 4 relative to the stopper body 2. Thus, for example, a latching means serving as the connecting means 7 can be designed such that the stopper body holder 4 and the stopper body 2 can be separated from each other by a quarter turn.

The membrane body 3 comprises a proximal facing area formed with an overall hood shape and comprising a flattened portion 10 in the center. At the transition area to the outer circumferential area of the membrane body 3, a proximal sealing element 8 is provided, formed for example as a circumferential swelling. Two further, substantially identically formed sealing elements 9 are provided distally downstream of the proximal sealing element 8. In accordance with FIG. 1, the sealing elements 8, 9 engage with correspondingly formed circumferential indentations 27 on the outer circumference of the stopper body 2, such that the membrane body 3 is attached to the stopper body 2, axially secured. As shown in FIG. 1, the distal end of the cap-like membrane body 3 substantially terminates in the distal end of the stopper body 2.

At least the sealing elements 8, 9 of the membrane body 3 are formed from an elastic material, for example an elastic plastic or rubber material. The outer circumference of the membrane body 3 is slightly larger, at least in the area of the sealing elements 8, 9, than the inner diameter of the product container (not shown), into which the piston stopper 1 is to be inserted. The sealing elements 8, 9 thus seal the product container off from the piston stopper by elastic distortion, such that the stopper body 2 does not come in direct contact with the product stored in the product container. Thus, only the membrane body 3 needs to be adapted to the product, for example suitable for medicines, but not the other elements of the piston stopper, in particular not the stopper body 2 and/or the stopper body holder 4.

While the proximal facing area of the membrane body 3 can in principle also be formed from an inelastic material, the entire membrane body 3 is preferably formed from an elastic material. Since the thickness of the membrane material on the entire proximal facing area of the stopper body 2 is comparatively thin, axially advancing the piston stopper 1 causes at most a negligible elastic distortion of the membrane body 3. This enables the product to be precisely dosed and/or the pressure to be precisely monitored, in accordance with the invention.

The stopper body 2 and the stopper body holder 4 are preferably made of an inflexible material, particularly preferably an inflexible plastic material such as polypropylene (PP), Rexen 13-R9A or other suitable material. In this way, the advancing force of the driven member (not shown) can be conducted via the stopper body holder 4 and the stopper body 2, substantially without loss, in order to deliver the product. In order to conduct the force without loss, the distal sections of the stopper body 2 rest full-face on the base area 5 at the proximal end of the stopper body holder 4. The stopper body 2 and the stopper body holder 4 also abut each other full-face at the proximal end 6 of the connecting means 7.

The membrane body 3 is non-detachably fitted on the stopper body 2. The inner diameter of the membrane body 3 in its resting state is preferably slightly smaller than the outer diameter of the proximal end of the stopper body 2. In this way, the membrane body 3 is expanded when placed onto the stopper body 2. The proximal facing area of the membrane body 3 in particular expands, such that the membrane body 3 can hardly be elastically distorted further in the area of the proximal facing area.

FIG. 2 shows a side view and a cross-section of a second embodiment of a piston stopper 1 in accordance with the present invention. This piston stopper 1 additionally comprises a rod-shaped force transferring means 11 which is mounted, in one embodiment, preferably centrally, in the stopper body holder 4, axially movably. The proximal end of the force transferring means 11 protrudes through a correspondingly formed axial opening in the stopper body 2 and directly abuts the inner side of the membrane body 3 in the area of the flattened portion 10. In principle, an intermediate body can also be provided in the contact area between the force transferring means 11 and the inner area of the membrane body 3, for example to increase the contact area or to spread the force.

The force transferring means 11 can be axially moved in the direction of the arrow and transfers the axial component of the pressure forces acting on the membrane body 3 onto a sensor (not shown), which detects the pressure exerted on force transferring means 11 and/or the membrane body 3 or the axial adjustment of the force transferring means 11, which will be explained in more detail below with reference to FIGS. 4 to 9. The force transferring means 11 is made of suitable inflexible material, for example an inflexible plastic such as polypropylene, or a metal such as aluminum or brass, or a ceramic, and is thus in practice not distorted when the piston stopper 1 is axially advanced.

FIG. 3 schematically shows a side view and a cross-section of a modification of the piston stopper 1 in accordance with a second embodiment of the present invention. Here, the stopper body 2 comprises an indentation or flattened portion, preferably formed rotationally symmetrically, in the area of the center on its proximal end, such that the proximal end of the force transferring means 11 protrudes beyond the base of the indentation 12 by the path length indicated by x. The maximum axial adjusting path of the force transferring means 11 is expediently selected such that it maximally corresponds to the path length x. Thus, with this modification, pressure forces acting on the membrane body 3 are reliably conducted to the sensor (not shown).

FIGS. 4 to 7 schematically show a cross-section of the proximal end of the stopper body holder 4 in accordance with the second embodiment of the present invention. In accordance with FIG. 4, the proximal end 6 of the stopper body holder 4 comprises an axial continuation 15, on the facing side of which a pressure sensor 13 is arranged. The pressure sensor 13 directly abuts the inner side of the membrane body 3 in accordance with FIGS. 2 and 3 via its proximal facing side, and thus measures the pressure acting on the membrane body 3. In one embodiment, the pressure sensor 13 is preferably a piezo-electric pressure sensor. The detected signals are conducted to a pressure monitoring means (not shown) via the wires 14, guided for example axially in the stopper body holder 4. In this embodiment, the height of the axial continuation 15 and the pressure sensor 13 is adapted to the height of the stopper body 2, such that the pressure sensor 13 protrudes only slightly beyond the facing area of the stopper body 2 or terminates substantially flush with the facing area of the stopper body 2. In the case of the modification in accordance with FIG. 3, the facing side of the pressure sensor 13 substantially terminates in the base of the indentation 12 or protrudes only slightly beyond it.

Figure 5:
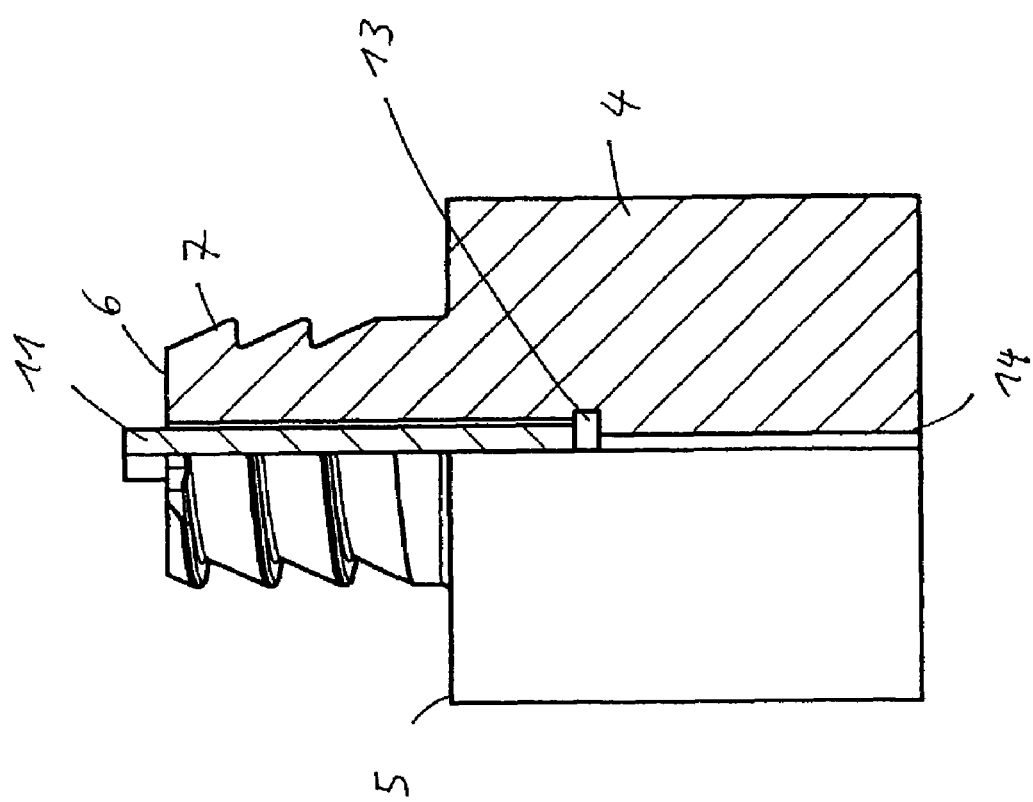
FIG. 5 shows a variant of the stopper body holder in accordance with the second embodiment.

In the modification in accordance with FIG. 5, the pressure sensor 13 is attached to the base of an axial receptacle in the proximal end of the stopper body holder 4, said receptacle accommodating the rod-shaped force transferring means 11, axially movably As shown in FIG. 5, the force transferring means 11 protrudes beyond the facing area 6 of the stopper body holder 4. The proximal end of the force transferring means 11 protrudes through the axial opening of the stopper body 2 shown in FIGS. 2 and 3, such that the facing area of the force transferring means 11 abuts, directly or mediated by an intermediate piece (not shown), the inner area of the membrane body 3 in the area of the flattened portion 10. In this way, the force transferring means 11 conducts the pressure forces acting on the membrane body 3 onto the pressure sensor 13.

Figure 6:
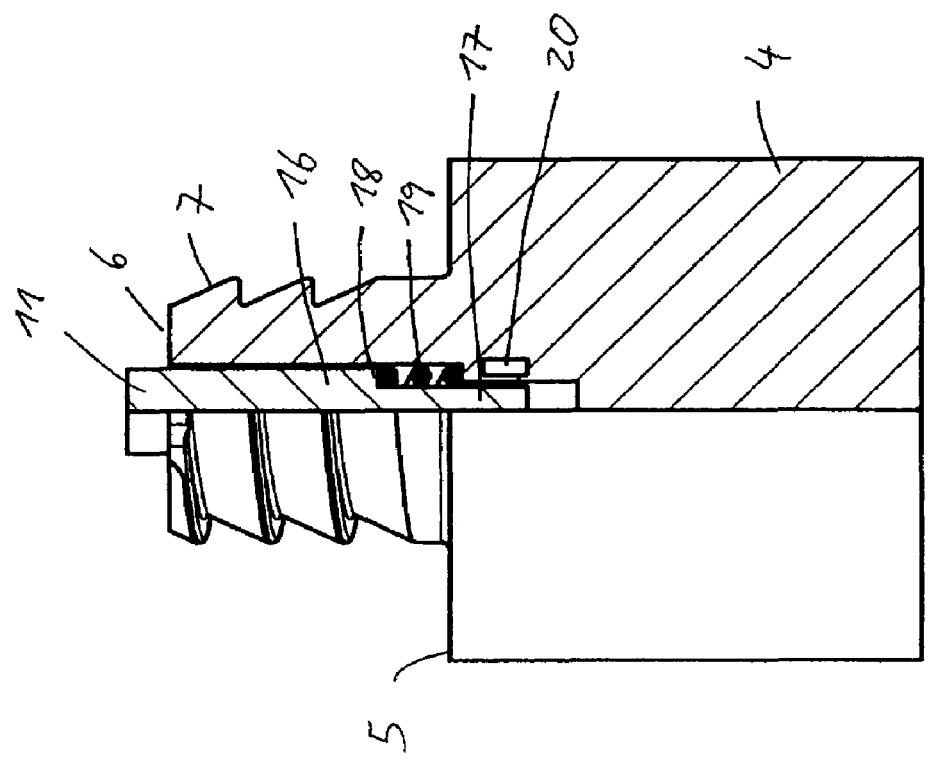
FIG. 6 shows another modification of the stopper body holder in accordance with the second embodiment.

In the modification in accordance with FIG. 6, an axial adjustment of the force transferring means 11 is detected with the aid of the schematically shown sensor 20 which measures the plunging depth of the distal end 17 of the force transferring means 11 into the receptacle of the stopper body holder 4. For this purpose, the receptacle in the stopper body holder 4 is formed stepped, with a comparatively wide receptacle towards the proximal end 6, to which a narrower receptacle is connected, the sensor 20 being arranged on the distal base of said narrower receptacle. The force transferring means 11 is mounted in the receptacle, axially movably, and is returned towards the proximal end 6 of the stopper body holder 4 by a restoring means, for example the schematically shown pressure spring 19. For this purpose, the force transferring means 11 comprises a wider section 16 proximally and a narrower section 17 distally, connected to each other via a collar section 18. The pressure spring 19 is supported on the collar against the corresponding collar of the receptacle of the stopper body holder 4. Axial pressure forces cause the force transferring means 11 to slide axially into the receptacle of the stopper body holder 4. The sensor 20 detects the plunging depth of the narrow end 17 of the force transferring means 11.

Figure 7:
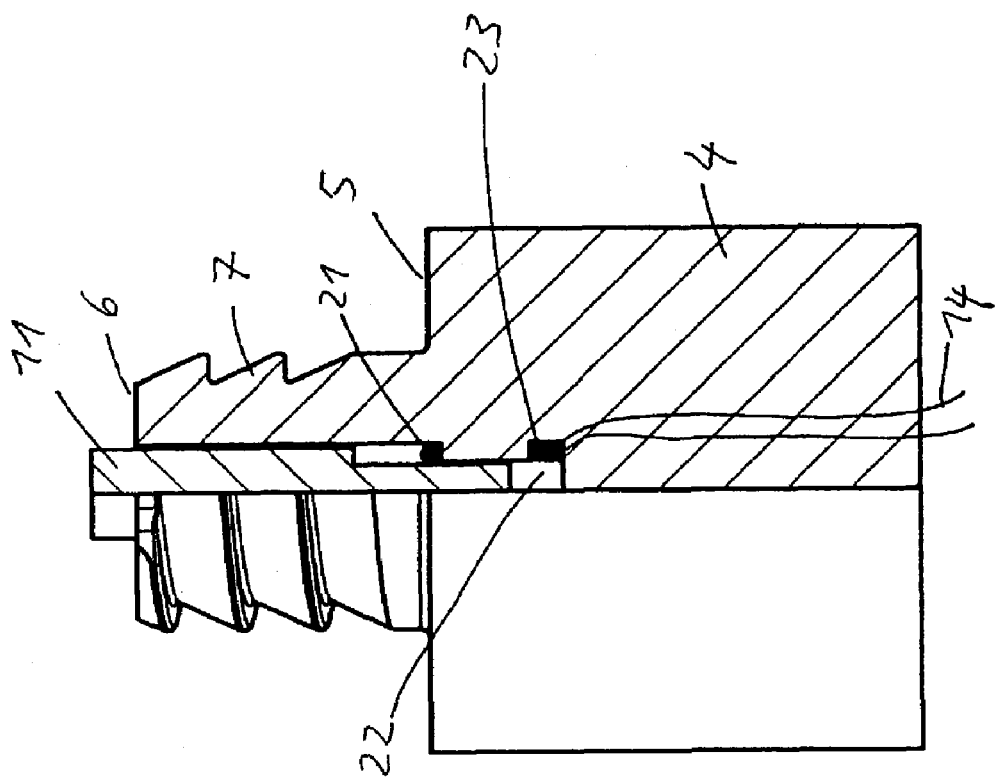
FIG. 7 shows another modification of the stopper body holder in accordance with the second embodiment.
Figure 8:
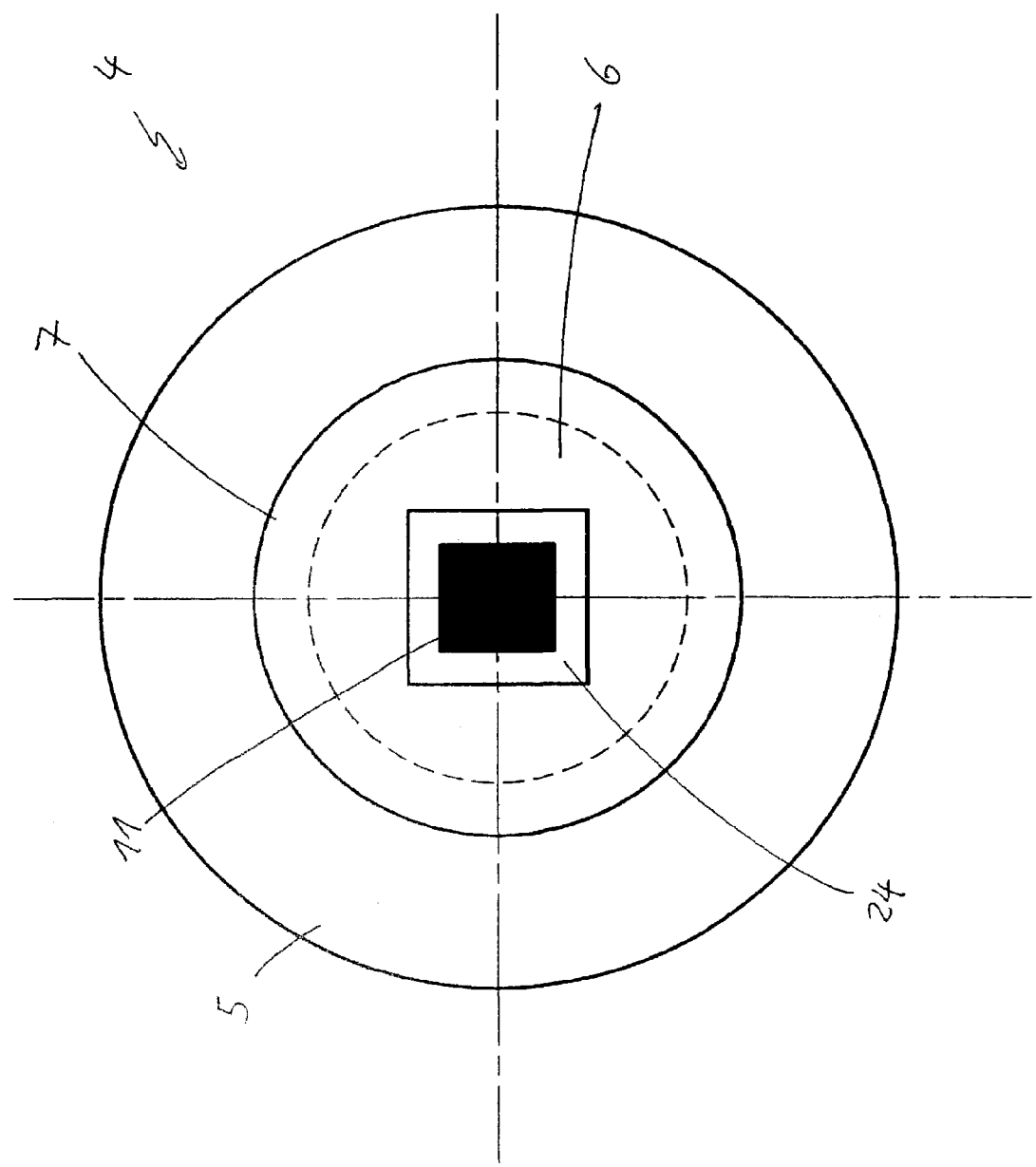
FIG. 8 shows a stopper body holder in accordance with FIGS. 5 to 7, in a schematic top view, said stopper body holder additionally comprising an anti-rotation device for the force transferring means.
Figure 9:
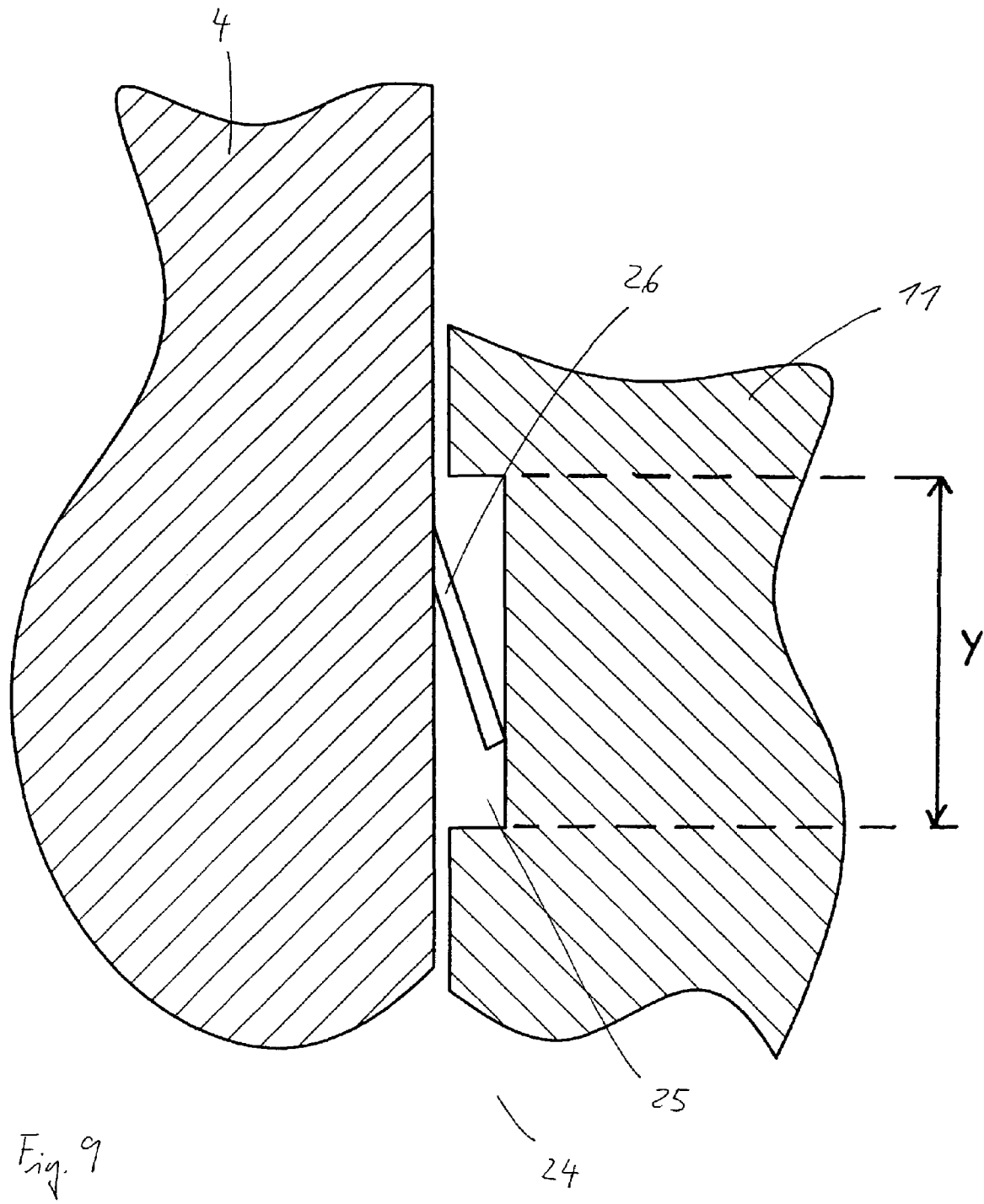
FIG. 9 shows an anti-loss device for the stopper body holder in accordance with FIGS. 5 to 8, in a schematic, enlarged cross-section.

In the modification in accordance with FIG. 7, the distal end of the force transferring means 11 plunges into a fluid chamber 22 in the stopper body holder 4. The fluid chamber 22 is sealed off from the force transferring means 11 fluid-proof, with the aid of the sealing means 21, for example an O-ring made for example of Viton or other suitable material. A fluid (not shown) is situated in the fluid chamber 22, for example a substantially non-compressible liquid or a gas. The force transferring means 11 is mounted, axially movably, in the receptacle of the stopper body holder 4 and also in the sealing means 21. Retracting the force transferring means 11 in the distal direction results in an increase in pressure in the fluid chamber 22 which is detected by the pressure sensor 23.

As shown in FIGS. 1 to 3, the piston stopper 1 in accordance with the present invention substantially comprises two portions, namely the stopper body 2 onto which the membrane body 3 is placed like a cap and connected to it, and the stopper body holder 4 which supports the stopper body 2 together with the membrane body 3. The rigid connection between the stopper body holder 4 and the stopper body 2 can be released by releasing the connecting means 7. The connecting means 7 is shown as a screw thread in FIGS. 1 to 3. In principle, a simple latching mechanism can suffice, for example a bayonet mechanism which can be released by turning it. In order that the sensor and/or the force transferring means is not unintentionally torn off or loosened when the connection between the stopper body holder 4 and the stopper body 2 is released, the force transferring means 11 is mounted in the stopper body holder 4, secured against rotation. This is shown schematically in the top view, in accordance with FIG. 8, onto a piston stopper in accordance with the second embodiment of the present invention. The receptacle 24 in the stopper body holder 4 for accommodating the force transferring means 11 is formed rotationally asymmetrical. In accordance with FIG. 8, the opening 24 exhibits a rectangular or quadratic cross-section, such that the force transferring means 11 cannot be rotated in the receptacle 24. In this way, the force transferring means 11 is mounted, linearly guided, in the stopper body holder 4.

When the connection between the stopper body holder 4 and the stopper body 2 is released, forces operate to pull the force transferring means 11 out of the receptacle 24. In order to prevent this, an axial anti-loss device can be provided, such that the force transferring means 11 is axially held in the receptacle 24, secured against loss. This is shown schematically in FIG. 9. The outer circumference of the force transferring means 11 comprises a radial recess 25 with which a snapping element 26 engages, such that the force transferring means 11 can no longer simply be pulled out of the opening 24. When the force transferring means 11 is distally plunged into the receptacle 24, the snapping element 26 presses against the inner circumferential area of the receptacle 24. As it is inserted into the radial recess 25, the snapping element 26, which is formed to be spring-elastic, is pushed back and thus holds the force transferring means 11, secured against loss. In principle, latching mechanisms and the like are also possible as the anti-loss device.

Figure 10:
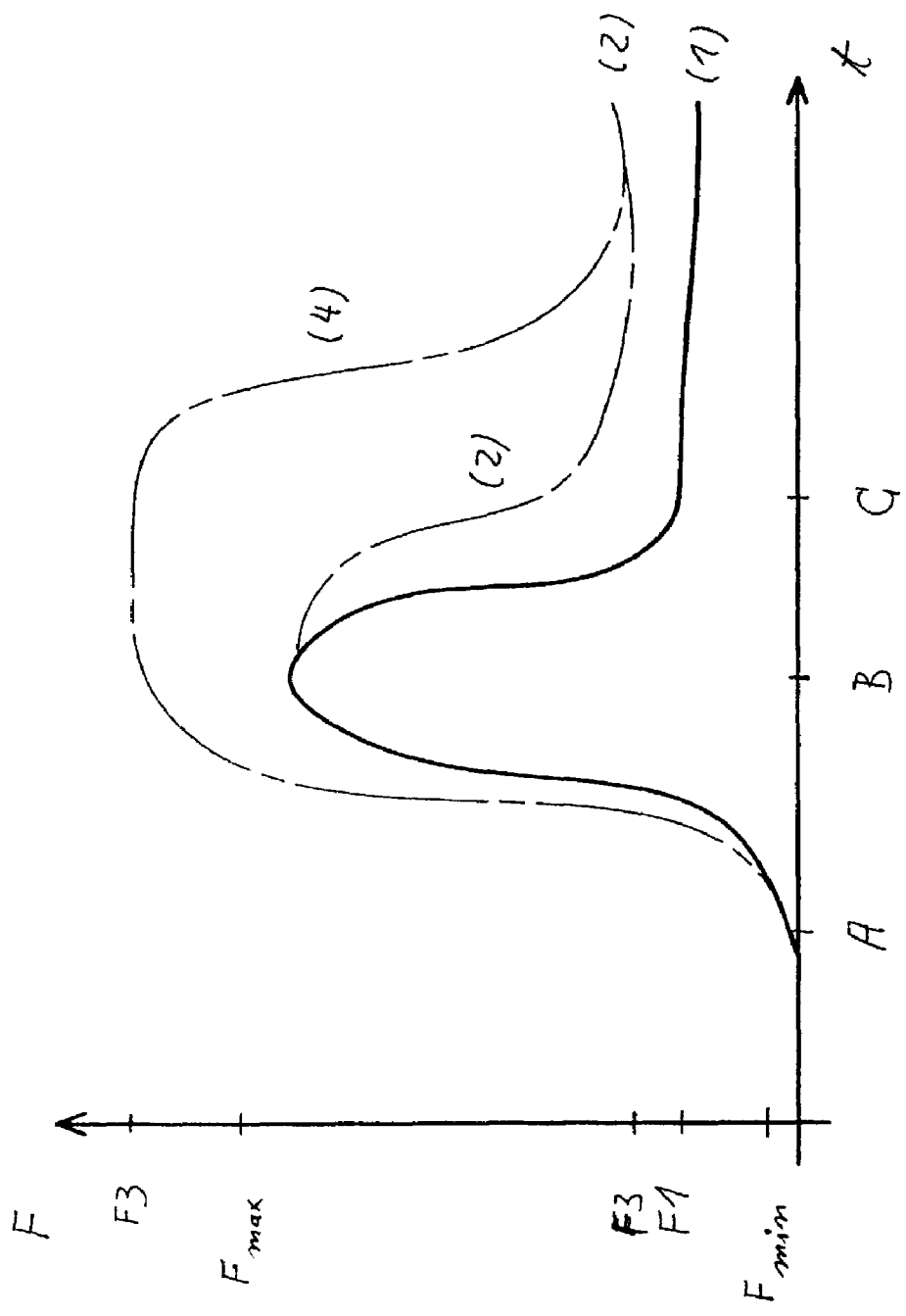
FIG. 10 shows the course over time of the pressure detected by the sensor in the piston stopper in accordance with the second embodiment.

FIG. 10 schematically shows the course over time of the pressure forces acting on the membrane body 3 when a product is delivered, which can be detected with the aid of the sensor in the piston stopper in accordance with the second embodiment of the present invention. In Curve (1), at Time A, a force is applied to a drive member of the injection device for axially advancing the piston stopper 1 for delivering a product. At Time B, the static frictional forces operating between the piston stopper 1 and the inner circumferential area of the product container are overcome. The force is then reduced to a level corresponding to the sliding frictional forces operating between the piston stopper 1 and the inner circumferential area of the product container. The magnitude of the force required for delivery is larger or smaller, depending on the flow cross-section of the delivery opening and any elements arranged downstream of said delivery opening, for example an injection needle. In Curve (2), for example, larger forces are required to deliver the product.

In the event of a blockage in the delivery opening of the product container, or in elements arranged downstream of said delivery opening, forces may accumulate which exceed the static frictional force between the piston stopper 1 and the product container. If the product is a substantially non-compressible liquid, the force curve rises essentially unchecked. If the blockage in the system is suddenly cleared, the pressure acting on the piston stopper 1 drops abruptly, causing a sudden discharge of a comparatively large dose.

The elastic ductility of the piston stopper 1 has an affect on the gradient of the curves shown. In the ideal case, in which the advancing force of the driven member of the injection device is transferred onto the piston stopper 1 without loss, the curves exhibit an almost rectangular rise. Elastic distortion of the piston stopper at Time B, i.e. when the static friction is exceeded, will result in a sudden discharge of a comparatively large dose of product. The more significantly the piston stopper 1 can be elastically distorted, the larger the observed peak in the time dependency of the product discharge.

As may be gathered from FIG. 10, the forces observed in the normal case move within particular limits. The forces exceed the upper limit in the event of a blockage in the system, and fall below the lower limit in the event of a leak in the system. Pre-setting suitable threshold values, therefore, can ensure that the injection device operates reliably. In the case of an injection device with a piston stopper in accordance with the second embodiment, for instance, a pressure monitoring means can be provided for monitoring the pressure acting on the membrane body 3. By pre-setting suitable threshold values $F_{min}$ and $F_{max}$ and comparing the measured pressure forces with the threshold values, a warning means of the injection device can generate a warning signal when the pressure detected by the sensor in accordance with the second embodiment exceeds or falls below a pre-settable threshold value. This also applies correspondingly when the sensor in accordance with FIG. 6 measures the adjusting path of the force transferring means 11.

Even where the piston stopper 1 is shown as rotationally symmetrical in the figures, a product container in accordance with the present invention can also in principle be formed rotationally asymmetrical, and can for example exhibit a rectangular cross-section with a correspondingly formed piston stopper. A product container in accordance with the present invention is suitable for storing medical or therapeutic products, for example liquids comprising medical or therapeutic active agents. A particularly preferred use relates to storing insulin for treating diabetic patients.

An injection device in accordance with the present invention can be hand-operated, for example in the form of a piston syringe or an injection pen, or the piston stopper can be advanced using motors, for example in the case of a miniature pump. A preferred application in the latter case relates to quasi-continuously administering micro-doses of insulin, in order to continuously monitor and adjust the blood sugar level of diabetic patients, by administering insulin.

In the foregoing description, exemplary embodiments, including exemplary preferred embodiments, of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A piston stopper for an injection device, for injecting a medical or therapeutic product by axially advancing said piston stopper into a product container, comprising:
   a stopper body;
   a stopper body holder connected to a driven member of said injection device;
   at least one sealing element for sealing off said product container from said stopper body, wherein a membrane body is connected to a proximal end of the stopper body, such that the stopper body does not come in contact with the product to be injected, said membrane body comprises said at least one sealing; and
   a sensor coupled to the stopper body holder for detecting the pressure exerted by the product on a proximal end of the membrane body, wherein the sensor comprises a force transferring means that protrudes through an opening in the stopper body holder at a proximal end and extends axially through an opening of said stopper body and abuts an inner side of the membrane body.

2. The piston stopper as set forth in claim 1, wherein the stopper body is formed from a generally inflexible plastic material and the membrane body is formed from a generally elastic material.

3. The piston stopper as set forth in claim 1, wherein the inner diameter of the membrane body in its resting state is smaller than the outer diameter of the proximal end of the stopper body, such that the membrane body is placed, radially expanded, onto the proximal end of the stopper body.

4. The piston stopper as set forth in claim 1, wherein said sealing element is formed on the outer circumference of the membrane body as a circumferential swelling of the membrane body which engages with a corresponding circumferential indentation on the outer circumference of the stopper body.

5. The piston stopper as set forth in claim 1, wherein the force transferring means is secured against rotation in the stopper body holder.

6. The piston stopper as set forth in claim 1, wherein the force transferring means is held in the axial direction, secured against loss by a securing means in the stopper body holder.

7. The piston stopper as set forth in claim 1, wherein an indentation is provided at the proximal end of the stopper body, and the force transferring means protrudes beyond the indentation to abut the inner side of the membrane body.

8. The piston stopper as set forth in claim 1, wherein the sensor is a pressure sensor.

9. The piston stopper as set forth in claim 8, wherein the pressure sensor measures a pressure in a fluid chamber of the stopper body holder, and said fluid chamber comprises at least one sealing element in order to seal off the fluid chamber from the force transferring means protruding into the fluid chamber.

10. The piston stopper as set forth in claim 1, wherein the sensor measures an axial adjustment of the force transferring means in the stopper body holder.

11. The piston stopper as set forth in claim 1, wherein the stopper body holder comprises a connecting means for connecting the stopper body holder rigidly to the stopper body.

12. The piston stopper as set forth in claim 1, wherein the stopper body consists of polypropylene and the membrane body consists of bromobutyl caoutchouc.

13. An injection device for administering a medical or therapeutic product, comprising a piston stopper which can be axially advanced into a container for the product to be administered in order to force out the product, the piston stopper comprising:
   a stopper body;
   a stopper body holder connected to a driven member of said injection device;
   at least one sealing element for sealing off said product container from said stopper body, wherein a membrane body is connected to a proximal end of the stopper body, such that the stopper body does not come in contact with the product to be injected, said membrane body comprising said at least one sealing element; and
   a sensor coupled to the stopper body holder for detecting the pressure exerted by the product on a proximal end of the membrane body, wherein the sensor comprises a force transferring means that protrudes through an opening in the stopper body holder at a proximal end and extends axially through an opening of said stopper body and abuts an inner side of the membrane body.

14. The injection device as set forth in claim 13, further comprising a pressure monitoring means for monitoring a pressure detected by the sensor.

15. The injection device as set forth in claim 14, further comprising a warning means for generating a warning signal when the pressure exceeds or falls below a pre-settable threshold value.

16. A piston stopper for an injection device, for injecting a medical or therapeutic product by axially advancing said piston stopper into a product container, comprising:
- a stopper body, wherein an indentation is provided at the proximal end of the stopper body;
- a stopper body holder connected to a driven member of said injection device;
- at least one sealing element for sealing off said product container from said stopper body, wherein a membrane body is connected to a proximal end of the stopper body, such that the stopper body does not come in contact with the product to be injected, said membrane body comprises said at least one sealing element; and
- a sensor coupled to the stopper body holder for detecting the pressure exerted by the product on a proximal end of the membrane body, wherein the sensor comprises a force transferring means that protrudes through an opening in the stopper body holder at a proximal end and extends axially through an opening of said stopper body, such that the force transferring means protrudes through the indentation at the proximal end of the stopper body by a length of an axial adjusting path of the force transferring means and abuts an inner side of the membrane body.

* * * * *